(12) United States Patent
Haecker et al.

(10) Patent No.: US 9,592,376 B2
(45) Date of Patent: Mar. 14, 2017

(54) HOLDING APPARATUS FOR HOLDING AT LEAST ONE TUBE CLAMP ON A MEDICAL TUBE, MEDICAL TUBE AS WELL AS METHOD FOR STERILIZING A MEDICAL TUBE

(75) Inventors: Juergen Haecker, Neu-Anspach (DE); Lothar Leick, Merzig-Ballem (DE); Wolfgang Schulz, St. Wendel (DE); Edmund-Jakob Thiry, Tholey (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 0 days.

(21) Appl. No.: 13/559,725

(22) Filed: Jul. 27, 2012

(65) Prior Publication Data

US 2013/0026396 A1 Jan. 31, 2013

Related U.S. Application Data

(60) Provisional application No. 61/512,958, filed on Jul. 29, 2011.

(30) Foreign Application Priority Data

Jul. 29, 2011 (DE) .................. 10 2011 110 474

(51) Int. Cl.
*A61M 39/28* (2006.01)
(52) U.S. Cl.
CPC ...... *A61M 39/284* (2013.01); *Y10T 29/49998* (2015.01)
(58) Field of Classification Search
CPC ................ A61M 39/284; Y10T 29/49998

USPC ............................................... 251/9, 10
See application file for complete search history.

(56) References Cited

U.S. PATENT DOCUMENTS

| 989,503 | A | * | 4/1911 | Hildebrand | .................. 222/517 |
|---|---|---|---|---|---|
| 1,610,622 | A | * | 12/1926 | Shaweker | ......................... 604/7 |
| 2,682,874 | A | * | 7/1954 | Hickey | ......................... 604/412 |
| 2,722,932 | A | * | 11/1955 | Hickey | ......................... 604/412 |
| 3,100,102 | A | * | 8/1963 | De Haan | ......................... 251/9 |
| 3,881,640 | A | * | 5/1975 | Noble | ......................... 222/158 |
| 4,643,389 | A | * | 2/1987 | Elson et al. | .................... 251/10 |
| 5,522,516 | A | * | 6/1996 | Duggal | ..................... A61J 9/00 215/11.4 |
| 2001/0049507 | A1 | * | 12/2001 | Ishida | ................ A61M 5/3273 604/250 |
| 2005/0253390 | A1 | | 11/2005 | Blazek | |
| 2007/0225684 | A1 | | 9/2007 | Wentling et al. | |
| 2009/0030378 | A1 | | 1/2009 | Garcia, Jr. | |

(Continued)

FOREIGN PATENT DOCUMENTS

| CN | 101801444 A | 8/2010 |
|---|---|---|
| DE | 7809912 U1 | 7/1978 |

(Continued)

*Primary Examiner* — Marina Tietjen
*Assistant Examiner* — Daphne M Barry
(74) *Attorney, Agent, or Firm* — Fish & Richardson P.C.

(57) ABSTRACT

A holding apparatus for holding at least one tube clamp on a medical tube, the tube clamp including at least one, usually two, clamping section(s) for altering a luminal cross-section of a medical tube during use, includes at least one receiving structure for detachably receiving at least one section of the tube clamp. A medical tube with at least one holding apparatus as well as a method for sterilizing a medical tube are also described.

10 Claims, 2 Drawing Sheets

(56) References Cited

U.S. PATENT DOCUMENTS

2010/0211016 A1* 8/2010 Palmer-Felgate ............ 604/192

FOREIGN PATENT DOCUMENTS

| | | |
|---|---|---|
| DE | 3324699 C1 | 12/1984 |
| EP | 0186509 A2 | 7/1986 |
| EP | 1905478 A2 | 4/2008 |
| JP | 2001527441 A | 12/2001 |
| JP | 0003123147 U | 7/2006 |
| JP | 2008518691 A | 6/2008 |
| WO | 98-48872 A1 | 11/1998 |
| WO | 03-030962 A2 | 4/2003 |

* cited by examiner

HOLDING APPARATUS FOR HOLDING AT LEAST ONE TUBE CLAMP ON A MEDICAL TUBE, MEDICAL TUBE AS WELL AS METHOD FOR STERILIZING A MEDICAL TUBE

CROSS-REFERENCES TO RELATED APPLICATIONS

The present application claims priority to U.S. Provisional Application No. 61/512,958, filed on Jul. 29, 2011, and claims priority to Application No. DE 10 2011 110 474.0, filed in the Federal Republic of Germany on Jul. 29, 2011, each of which is expressly incorporated herein in its entirety by reference thereto.

FIELD OF INVENTION

The present invention relates to a holding apparatus for holding at least one tube clamp. It further relates to a medical tube as well as a method for sterilizing a medical tube.

BACKGROUND INFORMATION

From practice, tube clamps with a mechanical effect for medical tubes such as infusion lines, blood circuits, but also for tubes used in laboratories are known. Such tube clamps fit tightly on the exterior of the tube. They may be manually taken into an open position in which they do not hinder the fluid flow in the tube, or into a closed position in which they reduce or stop the fluid flow, e.g., by squeezing or clamping the tube. Therefore, tube clamps serve as mechanical control systems for the flow of medical fluids through the tube, e.g., of blood, infusion solutions such as isotonic solutions, and medication.

SUMMARY

One object of the present invention is to propose a holding apparatus for holding at least one tube clamp on a medical tube. Additionally, a medical tube with at least one holding apparatus according to the present invention as well as a method for sterilizing a medical tube according to the present invention are to be specified.

According to the present invention, a holding apparatus for holding at least one tube clamp on a medical tube is therefore proposed, wherein the tube clamp comprises at least one, two or more clamping sections for altering a luminal cross-section of a medical tube in or during use. The holding apparatus comprises at least one receiving structure for removably receiving at least one section of the tube clamp.

The medical tube according to the present invention (in short, also: tube) comprises at least one holding apparatus according to the present invention.

The method according to the present invention serves to sterilize a medical tube which comprises at least one tube clamp that has at least two clamping sections for altering a luminal cross-section of the medical tube. The tube has at least one holding apparatus—which is in particular designed according to an exemplary embodiment as described herein—which comprises at least one receiving structure for detachably receiving at least one section of the tube clamp. The method encompasses placing the tube clamp into a parking position at the holding apparatus, in which the received section of the tube clamp is arranged in or on the receiving structure. Further, the method encompasses joint sterilization of the tube and the tube clamp that was placed into the parking position.

Exemplary embodiments according to the present invention may comprise one or more of the features described herein.

In all of the following exemplary embodiments, the use of the expression "may be" or "may have" and so on, is to be understood synonymously with "preferably is" or "preferably has," respectively, and so on, and is intended to illustrate an exemplary embodiment according to the present invention.

In certain exemplary embodiments according to the present invention, the embodied clamping sections are of the same kind. In other exemplary embodiments according to the present invention, at least one first clamping section and one second clamping section are designed to be different from each other.

Altering a luminal cross-section of a medical tube is, in some exemplary embodiments according to the present invention, a pinching-off or squeezing. This may at least reduce, completely stop or prevent a volume flow for a medical fluid along the lumen of the tube.

In certain exemplary embodiments according to the present invention, detachably receiving at least one section of the tube clamp is or encompasses meshing, catching, clamping and/or snapping.

The holding apparatus according to the present invention is or comprises at least one tube connector in some exemplary embodiments.

The tube connector is in some exemplary embodiments according to the present invention embodied as an arterial and/or venous patient connector of an extracorporeal blood tube set, in particular as a connector on or to which each of the arterial and/or the venous needle is/are connected.

A needle is in certain exemplary embodiments according to the present invention understood as the patient needle together with a puncture wing (butterfly) and a part of the tube and a corresponding connector half.

In some exemplary embodiments, the holding apparatus according to the present invention is or at least comprises a tube cap.

The tube connector and/or the tube cap are in certain exemplary embodiments according to the present invention not moveable along the tube during use.

The holding apparatus, tube connector and/or tube cap are in certain exemplary embodiments according to the present invention an integral or a non-integral component of a blood cassette or a tube set.

In some exemplary embodiments according to the present invention of the holding apparatus, the section of the tube clamp which is detachably received by the receiving structure is or at least comprises at least one clamping section.

In certain exemplary embodiments according to the present invention, detachably receiving the tube clamp or a section hereof on the holding apparatus means that the whole tube clamp may be completely separated or disconnected from the holding apparatus during use of the tube. This is in some exemplary embodiments according to the present invention possible by the fact that the tube clamp is pushed down from the holding apparatus along the tube.

The receiving structure is in some exemplary embodiments according to the present invention geometrically fit to a section of the tube clamp, e.g., to the present clamping sections, such that the tube clamp remains in the parking position and/or at least cannot move along the tube without anybody being involved each during the sterilization process or during storage.

In certain exemplary embodiments according to the present invention, the holding apparatus and/or its receiving structure is provided for not enabling (or preventing) an alteration of the luminal cross-section of the tube, in particular in its flexible line section, by means of the tube clamp as long as it is in the parking position.

In some exemplary embodiments according to the present invention of the holding apparatus, the receiving structure is embodied as or at least comprises at least one recess encircling the holding apparatus—its whole circumference or only one or several sections of the circumference.

In certain exemplary embodiments according to the present invention, the receiving structure of the holding apparatus is separated or divided from the holding apparatus.

In some exemplary embodiments according to the present invention, the section of the tube which holds or supports the holding apparatus is differently built than at least one section of the tube adjacent thereto.

In certain exemplary embodiments according to the present invention of the holding apparatus, it comprises an anti-rotation or anti-twist protection. This allows for a rotating or twisting of the tube clamp around a longitudinal axis of the holding apparatus only to a limited extent, or it completely prevents such rotating or twisting.

Such anti-rotation or anti-twist protection may comprise stops, limitations, grooves, slots, elevations and the like.

In some exemplary embodiments according to the present invention, the recess of the receiving structure is or at least comprises a groove or a slot.

In some exemplary embodiments of the holding apparatus according to the present invention, the receiving structure is or at least comprises at least one elevation encircling the holding apparatus—its whole circumference or only one or several sections of the circumference.

The recess and/or the elevation are in certain exemplary embodiments according to the present invention—in particular completely or basically—ring-shaped.

The term ring-shaped is in some exemplary embodiments according to the present invention not only understood to be shapes that are continuous along a circumference of the holding apparatus. Rather, also shapes that have one or more gaps are included.

In certain exemplary embodiments according to the present invention, the receiving structure comprises a combination of recess(es) and elevation(s). It may for example comprise two elevations and one recess. These may, e.g., be arranged in the sequence: elevation, recess, elevation, in the longitudinal direction of the holding apparatus or in the longitudinal direction of the tube one after the other.

In some exemplary embodiments, the holding apparatus according to the present invention comprises at least one tube clamp according to the present invention. It may also comprise, e.g., two or more tube clamps according to the present invention. If the holding apparatus according to the present invention comprises several tube clamps according to the present invention, it can also comprise several receiving structures.

The holding apparatus according to the present invention is or was in some exemplary embodiments sterilized together with or jointly with the tube clamp.

The holding apparatus may completely or partially be made of the same material as the tube. In certain exemplary embodiments according to the present invention, the holding apparatus is made of a harder material than the tube or than its—mostly flexible, which here is to be understood as bendable and/or compressible by means of the tube clamp—line sections.

In particular, in certain exemplary embodiments of the medical tube according to the present invention, the holding apparatus or at least a section hereof are made of or comprise a first material. The tube or at least a section of the tube is made of or comprises a second material.

The first and the second material differ from each other. The section of the tube may in particular be a flexible line section which during use may be or should be clamped by means of the tube clamp.

In some exemplary embodiments according to the present invention, the first material of the holding apparatus is harder or more pressure-resistant than the second material of the tube.

In certain exemplary embodiments according to the present invention, the tube clamp is movable or slidable along the axis of the tube during use of the tube, preferably freely movable or slidable. In some exemplary embodiments according to the present invention, the tube clamp may be used as intended at a multitude of sections of the tube, i.e., for changing or closing of the lumen of the tube, preferably under any desired distance of the holding apparatus.

In particular exemplary embodiments according to the present invention, the tube clamp is usable as intended without any support from or interaction with the holding apparatus.

In some exemplary embodiments according to the present invention, at least one of the clamping sections is embodied and/or arranged to change the lumen of the tube by—preferably solely or essentially—radially, preferably directly, influencing the effect the clamp has on the tube or to prevent flow through the tube.

In certain exemplary embodiments according to the present invention, the holding apparatus is not a valve.

In some exemplary embodiments according to the present invention, the holding apparatus is not embodied for changing the lumen of the tube and/or supporting the same during its intended use.

In certain exemplary embodiments according to the present invention, the tube clamp does not comprise a lever extending from the tube clamp.

In some exemplary embodiments according to the present invention, the tube is embodied as an extracorporeal blood circuit or as a section hereof.

In some exemplary embodiments according to the present invention, the tube clamp is in an open state while it is being placed into a parking position on the holding apparatus.

In certain exemplary embodiments according to the present invention, the "joint" sterilization of the tube and the tube clamp that was placed into the parking position is to be understood as being performed simultaneously and/or with the same sterilization method. In some exemplary embodiments according to the present invention, "joint" sterilization is to be understood as the tube clamp being connected with the holding apparatus during sterilization.

The method according to the present invention encompasses in some exemplary embodiments placing at least one clamping section in, on or to the receiving structure before or for sterilizing the medical tube.

The holding apparatus may be embodied to be integral with the flexible line sections of the tube. It may, however, also be a separately produced element that was subsequently connected with the flexible line sections of the tube.

In exemplary embodiments in which the holding apparatus and the remaining sections of the tube are separate parts, it may be provided that sections of the tube, in particular flexible, conducting sections, or an end section hereof is/are introduced into an interior of the holding apparatus only so far that it does not reach under the receiving structure and/or under a recess for the clamping sections. In this exemplary embodiment, it is advantageously ensured that pressure exerted by the tube clamp cannot damage any section of the tube. This even applies if the pressure is intentionally or unintentionally very high.

In some exemplary embodiments according to the present invention, the holding apparatus cannot be moved along the longitudinal axis of the tube.

Some or all of the exemplary embodiments according to the present invention may comprise one or several of the advantages named above or hereafter.

In the closed position, the tube clamp according to the present invention exerts pressure over a section of the tube for functional reasons, in order to reach the desired fluid flow rate in the tube. It is known from practice that this pressure may damage the tube, at least after a certain period of time. But even in its open position, tube clamps may damage the tube or permanently alter it in its cross-section due to pressure. This may in particular take place during the joint sterilization of the tube and the tube clamp and/or during the subsequent storage. Such damage or alteration of the tube may lead to the development of leakages or of tube sections in which turbulences occur during use and/or that promote kinking of the tube. The latter may lead to the development of thrombi, clotting of certain fluids, occlusion of the tube and so on. In addition, the material damage may be hygienically critical as in certain cases the damage of the tube may create an entry for germs. Such damage and the consequences associated herewith may advantageously be prevented when using the present invention.

Exemplary embodiments of the present invention are explained below with reference to the accompanying drawings, in which identical reference numerals denote same or similar components.

DETAILED DESCRIPTION

Figure 1:
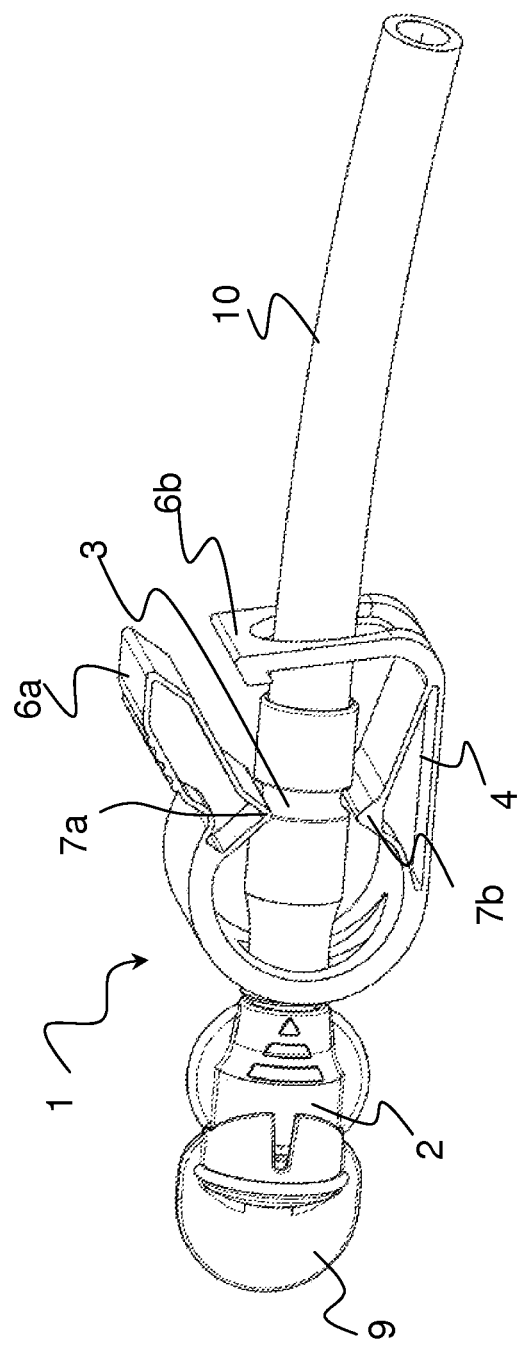
FIG. 1 shows a tube according to the present invention with a holding apparatus according to the present invention in a parking or sterilization position of a tube clamp which is connected with a tube.

FIG. 1 shows a medical tube 10 according to the present invention with a holding apparatus 1 according to the present invention and a flexible line section that is connected herewith (to the right in FIG. 1).

The holding apparatus 1 of FIG. 1 is merely exemplarily embodied as a tube connector by means of which the tube 10 is or will be connected with the patient's vascular system or with a medical device. The holding apparatus 1 comprises a connection section 2 for this purpose.

The holding apparatus 1 additionally comprises a receiving structure 3 for receiving a tube clamp 4 in a parking location or position (which herein is also denoted as resting or sterilization location or position). The tube clamp 4 is shown in such a parking position in FIG. 1. In this parking position, the tube clamp 4, which in the example of FIG. 1 covers or overlaps both parts of the holding apparatus 1 and a part of the flexible line section, is detachably connected with a section hereof with the holding apparatus 1. The tube clamp 4 comprises two snap-in devices 6a, 6b for closing or locking the clamp 4 during use. Further, the tube clamp 4 comprises two clamping sections 7a, 7b. In the example of FIG. 1, the tube clamp 4 is connected with or received in the receiving structure 3 by means of its clamping sections 7a, 7b. FIG. 1 further shows a detachable end cap 9 for the connection section 2 for preventing a contamination of the holding apparatus 1 until the use of the tube 10.

The tube 10 is passed through the tube clamp 4. The tube clamp 4 thus encompasses or grasps the tube 10. The two clamping sections 7a and 7b, which face each other, for clamping a tube section in between them mesh into the receiving structure 3.

The receiving structure 3 is embodied as a ring-shaped recess in FIG. 1, i.e., a recess which extends over the circumference of the holding apparatus 1. The cross-section of the recess may have any conceivable shape that is suitable for receiving or delimiting at least one section of the tube clamp 4. The cross-section of the recess may be, e.g., V-shaped, U-shaped, etc.

As the receiving structure 3 receives the clamping sections 7a, 7b of the tube clamp 4 when the tube clamp 4 rests in the parking position shown in FIG. 1, the receiving structure 3 prevents the tube clamp 4 from moving freely along the tube 10 during a sterilization process or during the subsequent storage of a tube 10. This way, the clamping sections 7a, 7b or a different section of the tube clamp 4 are prevented from clamping the tube 10 or even damaging it by means of pressure.

In FIG. 1, the tube 10 comprises exactly one holding apparatus 1. It is, however, also provided according to the present invention that a tube according to the present invention comprises several holding apparatuses. It is also provided to pinch off several tubes in more complicated tube systems, e.g., fluid line systems with several tubes 10 being coupled in parallel, as is the case with central venous catheters, by means of a holding apparatus 1 according to the present invention.

In the exemplary embodiment of FIG. 1, the holding apparatus 1 embodied as a connector comprises a screw mechanism on or at its connection section 2 for its connection. Alternatively or additionally, the connection section 2 may comprise each connection system known from the state of the art or each connection mechanism, e.g., a coupling mechanism or a rotation mechanism.

Figure 2:
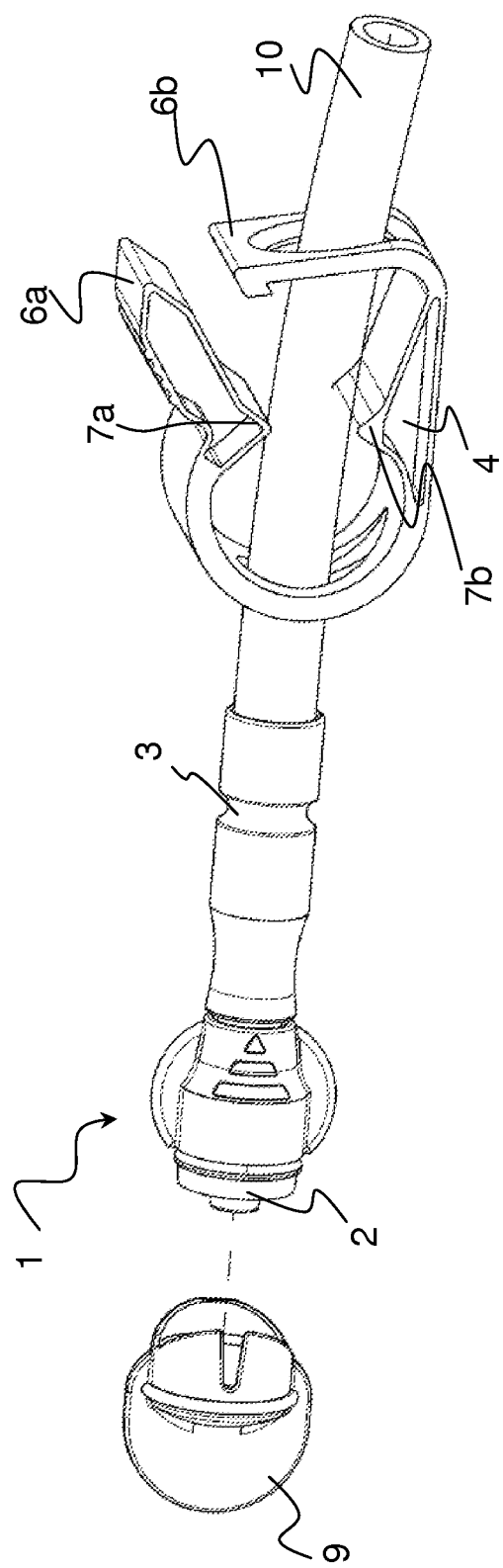
FIG. 2 shows the arrangement of FIG. 1 in an operating position of the tube.

FIG. 2 shows the arrangement of FIG. 1 in an operating position of the tube 10. The tube clamp 4 is no longer in the parking position on the holding apparatus 1. It is rather shifted towards a tube section on or at which its clamping effect is desired.

The end cap 9 is shown being detached from the connection section 2 in FIG. 2. In this state, the tube 10 may be connected with, e.g., a venous or arterial access of a patient, or with a connection piece of a medical device and so on.

During use, the two snap-in devices 6a, 6b of the tube clamp 4 are interlocked. The clamping sections 7a, 7b are then tightened towards each other and thus exert pressure on the tube 10 which is clamped in between. This way, the luminal cross-section of the tube 10 is altered. The flow rate of the fluid conducted in the tube 10 varies according to this change in luminal cross-section.

The illustrated exemplary embodiment of the tube clamp 4 in both figures is to be understood merely as an example. Other tube clamps known from the state of the art may, of course, also be held in a parking position by means of the holding apparatus 1 according to the present invention.

REFERENCE NUMERALS USED 1 holding apparatus as tube connector
2 connection section
3 receiving structure
4 tube clamp
6a, b snap-in device
7a, b clamping section
9 end cap
10 tube

What is claimed is:

1. A medical tube, comprising:
at least one holding apparatus and at least one tube clamp, wherein the holding apparatus and the tube clamp are configured to be separate components from one another, the holding apparatus configured to hold the at least one tube clamp on the medical tube, the tube clamp comprising at least one clasping section configured to at least one of reduce or completely stop a volume flow of a medical fluid along a lumen of the medical tube, wherein the tube clamp is movable along an axis of the medical tube, the holding apparatus comprising:
at least one receiving structure configured to:
detachably receive the at least one clamping section of the at least one tube clamp while the at least one tube clamp is in an open state, and
prevent the at least one clamping section from at least one of reducing or completely stopping the volume flow of the medical fluid along the lumen of the medical tube whenever the at least one clamping section of the at least one tube clamp is received by the at least one receiving structure,
wherein the at least one tube clamp is not longitudinally movable along the medical tube when the at least one clamping section is detachably received on the at least one receiving structure.

2. The medical tube according to claim 1, wherein the holding apparatus includes a tube connector.

3. The medical tube according to claim 1, wherein the holding apparatus includes a tube cap.

4. The medical tube according to claim 1, wherein the receiving structure includes at least one recess that encircles at least a section of the holding apparatus.

5. The medical tube according to claim 1, wherein the receiving structure includes at least one elevation that encircles at least a section of the holding apparatus.

6. The holding apparatus according to claim 1, wherein the holding apparatus is sterilized together with the tube clamp.

7. The medical tube according to claim 1, wherein at least a section of the holding apparatus is made of a first material, wherein at least a section of the tube is made of a second material, and wherein the first material differs from the second material.

8. The medical tube according to claim 7, wherein the tube is embodied as a section of an extracorporeal blood circuit.

9. A method for sterilizing a medical tube, the medical tube comprising at least one tube clamp which has at least one clamping section configured to at least one of reduce or completely stop a volume flow of a medical fluid along a lumen of the medical tube, and at least one holding apparatus with a receiving structure configured to detachably receive at least one section of the tube clamp while the at least one tube clamp is in an open state, wherein the tube clamp is movable along an axis of the medical tube, the method comprising:
placing the tube clamp into a parking position on the holding apparatus in which the section of the tube clamp is arranged one of in and on the receiving structure, the receiving structure preventing the at least one clamping section from at least one of reducing or completely stopping the volume flow of the medical fluid along the lumen of the medical tube whenever the section of the tube clamp is arranged one of in and on the receiving structure;
jointly sterilizing the tube and the tube clamp that was placed into the parking position;
wherein the section of the tube clamp which is detachably received by the receiving structure includes the at least one clamping section;
wherein the tube clamp is not longitudinally movable along the medical tube when the at least one clamping section is detachably received on the receiving structure; and
wherein the holding apparatus and the tube clamp are configured to be separate components from one another.

10. The method according to claim 9, further comprising placing the at least one clamping section one of into and onto the receiving structure one of before and for sterilizing the medical tube.

* * * * *

UNITED STATES PATENT AND TRADEMARK OFFICE
CERTIFICATE OF CORRECTION

| | | |
|---|---|---|
| PATENT NO. | : 9,592,376 B2 | Page 1 of 1 |
| APPLICATION NO. | : 13/559725 | |
| DATED | : March 14, 2017 | |
| INVENTOR(S) | : Juergen Haecker et al. | |

It is certified that error appears in the above-identified patent and that said Letters Patent is hereby corrected as shown below:

On the Title Page

Column 1 (75) Inventors, Line 2, delete "Merzig-Ballem" and insert --Merzig-Ballern--.

Signed and Sealed this
Second Day of May, 2017

Michelle K. Lee
*Director of the United States Patent and Trademark Office*